| United States Patent [19] | [11] 3,974,197 |
|---|---|
| Parliment | [45] Aug. 10, 1976 |

[54] NEW COLOR COMPOSITION

[75] Inventor: Thomas Holden Parliment, New City, N.Y.

[73] Assignee: General Foods Corporation, White Plains, N.Y.

[22] Filed: Apr. 7, 1975

[21] Appl. No.: 565,896

[52] U.S. Cl. .................... 260/439 R; 106/304; 106/288 Q; 426/540; 426/250; 260/429 J
[51] Int. Cl.² ........................................ C07F 15/02
[58] Field of Search............ 106/288 Q, 304, 308 Q, 106/22; 426/540, 250; 260/439 R

[56] References Cited

UNITED STATES PATENTS

| 2,127,374 | 8/1938 | Allen et al. .................... 106/304 |
| 2,445,770 | 7/1948 | Fischer ............................ 106/304 |

*Primary Examiner*—Winston A. Douglas
*Assistant Examiner*—J. V. Howard
*Attorney, Agent, or Firm*—Bruno P. Struzzi; Daniel J. Donovan; Doris M. Bennett

[57] ABSTRACT

The reaction of certain organic α-hydroxy carboxylic acids with ferric ions produces nutritive stable water soluble yellow colors suitable for use in food products.

8 Claims, No Drawings

3,974,197

NEW COLOR COMPOSITION

BACKGROUND OF THE INVENTION

The present invention relates to intense, stable yellow colors appropriate for use in edible systems and the method for producing the same. More specifically, the immediate invention relates to the discovery of new non-toxic yellow colors obtained by complexing certain organic hydroxy carboxylic acids and mixtures of these with ferric ions as contained in ferric salts.

The need for stable yellow colors of high intensity has existed for some time. This need has been accentuated in recent years due to an increased awareness of the need to further evaluate the physiological effects, if any, artificial colors have on the consumer. Since the number of artificial colors is limited and their safety questioned, and since natural pigments are both unstable and expensive, the need for new and improved coloring systems is apparent.

While it is generally known that ferric salts form complexes with certain phenolic compounds to form intense colors, as in ink, the fact that these same salts form complexes with specific organic α-hydroxy carboxylic acids to give intense stable yellow colors is new to the art.

SUMMARY OF THE INVENTION

I have found that organic α-hydroxy carboxylic acids having at least one and no more than two carboxyl groups for each hydroxyl group present and having a degree of conjugation not exceeding three double bonds when combined with a ferric salt complex therewith to form intense yellow coloring agents which are non-toxic, non-flavorful, water soluble, and in some instances, extremely stable.

Accordingly, the principle object of the present invention is to provide new and improved yellow coloring agents and to impart to certain foodstuffs containing the same—an intense yellow color.

DETAILED DESCRIPTION OF THE INVENTION

The iron complex colors of the immediate invention are formulated by combining at least equimolar amounts of a ferric salt or salts with certain α-hydroxy carboxylic acids or mixtures thereof. Intended for inclusion in this class of compounds are derivatives such as water soluble esters and ethers formed by chemical derivatization of other than the α-hydroxyl to the carboxyl group. Thus, hydroxyl groups other than the α-hydroxyl group may be esterified, etherified or eliminated all together in order to obtain derivatives of the original compound which still demonstrate yellow color and which are still water soluble. While a molar ratio of at least about 1:1 and up to about 1:3 ferric salt to acid respectively is considered optimum, ratios of acid higher than 1:3 may be employed although not considered necessary for the production of yellow color.

The α-hydroxy carboxylic acids which I have generally found to be effective in terms of yellow color production are those acids having preferably not more than one carboxyl group for each α-hydroxyl group and in no instance more than two carboxyls for each α-hydroxyl function. In addition, some conjugation is acceptable but more than three conjugated double bonds causes a shift in the lamda (λ) maximum to longer wavelengths (higher than 500 Millimicrons) making the visual hues less yellow and more prone toward the green and blue.

Accordingly, the preferred acids of this invention are those having 1 carboxyl for each α-hydroxyl function and no more than 3 conjugated double bonds such as quinic acid and mandelic acid. Exemplary of the corresponding quinic acid ethers and esters of the immediate invention are respectively, 1,4,5-trihydroxy, 3-acetoxy cyclohexane carboxylic acid, 1,3,5-trihydroxy, 4-acetoxy cyclohexane carboxylic acid, 1,3,4 trihydroxy cyclohexane, 5-acetoxy cyclohexane carboxylic acid, 3-methoxy 1,4,5-trihydroxy cyclohexane carboxylic acid, 4-methoxy, 1,3,5-trihydroxy cyclohexane carboxylic acid, and 5-methoxy, 1,3,4-trihydroxy cyclohexane carboxylic acid, as well as analogous compounds where the alkyl moiety of, for example, the ether or ester contain only as many carbons as to retain the water solubility of said ether or ester. The esters devoid of the acetoxy radical, where the acetic acid moiety is replaced by higher aliphatic acid, may also be employed. The sources of iron employed are generally those in which the iron is known to exist in the ferric state or ionize thereto on dissolution. For the best results, iron salts are employed, ferric chloride being the most satisfactory source of iron from both toxicity and solubility standpoints, ferric sulfate and ferric nitrate providing satisfactory color, ferric phosphate being least preferable due to the presence of phosphate itself and the inherent danger of complexation. Use of ferric chloride as the iron source is particularly preferred where it is to be employed in conjunction with the α-hydroxy carboxylic acid in an animal food where ferric chloride has already been FDA approved for use therein.

Since ferric ions interact with many food ingredients, the food system in which the coloring agents of this invention are to be employed should not contain ingredients known in the art to complex preferentially with iron such that the color complex of the immediate invention will be destroyed. This may include not only α-hydroxy carboxylic acids not claimed in this invention, e.g. citric acid, but acids intended for inclusion in this invention but which would preferentially complex with the iron over the α-hydroxy carboxylic acid employed in the foodstuff for the particular color desired. For example, quinic acid and mandelic acid are the preferred α-hydroxy carboxylic acids of the present invention since they contain only 1 carboxyl group for each α-hydroxy function and form the most intensely colored complexes. Malic, glycolic and dihydroxymaleic acids form good yellow colors but less intense colors on a molar basis. Therefore, although all of these acids form yellow color complexes where an intensely yellow-colored foodstuff is desired, the foodstuff containing the quinic acid or mandelic acid iron complexes should not contain a yellow color-producing α-hydroxy carboxylic acid which will preferentially complex with the iron such that the quinic or mandelic acid and iron complexes are destroyed resulting in a loss of color intensity. Exemplary of further compounds which should not be present in the foodstuff are reducing compounds such as ascorbic acid (Vitamin C), complexing agents such as phosphates, for example, monocalcium phosphates, aminopolycarboxylic acids such as ethylene-diamine tetraacetic acid and certain hydroxycarboxylic acids such as gluconic acid, citric acid, and tartaric acid, certain other known chelating agents such as nitrilotriacetic acid and ethyleneglycol-bis (beta-amino ethyl ether) N,N-tetra acetic acid to mention just a few. Note that while some α-hydroxy carboxylic acids other than the specifically claimed group of acids of this invention produced yellow color such as citric acid, only those having from 1 to 2 carboxyl group for every α-hydroxy group and containing no more than 3 double bonds, as well as their esters and ethers formed on other than the α-hydroxyl group, have been found to produce satisfactory stable color in the absence of strong sequestering agents, the quinic acid/iron complex being stable indefinitely in fluid form and consequently the preferred embodiment of this invention in terms of a stable intense liquid yellow color. Accordingly, food systems such as beverages in which these colors are to be employed should be reformulated to delete the reducing agent(s) and sequestering agent(s) present and make an adequate substitution, therefore, if necessary.

The color constitutents may be combined in any number of ways. Where the color is to be employed as a powder, the iron-complex color may be generated in aqueous solution and dried as by freeze drying, spray drying, drum drying or the like either by itself or on a water soluble carbohydrate, for example, a dextrin such as the commercially well-known Mor-Rex, polyglucose, invert sugars, and water soluble corn syrups solids to mention just a few. The dry colored powder possesses the hue of the generated color and this can be used, for example, where one wishes to color plate the product. Alternatively, the iron source or the acid may alone be dried on a water soluble non-reactive bulking agent such as a water soluble carbohydrate or any of the water soluble substances previously mentioned to derive a dry, colorless ferric or acid powder which will not react with the other non-fixed constituent of the color complex until both are placed together in solution. Whether one subsequently decides to reduce the particle size of any of the aforementioned dry powders for reasons of solubility or whatever, this may be done according to methods and parameters well known in the art. Still further, where the color is to be employed in a liquid system such as a liquid beverage, each component of the complex may be added either sequentially or concurrently to the same so that the complex is formed in situ or alternatively, the color complex may be formed in solution and then the solution added directly to the beverage. In either instance although obtention of color is relatively pH independent optimum color in a beverage is obtained at an acidic pH of preferably about 3 to 4 and where the quinic acid/iron complex is employed.

The following examples are intended to illustrate the best mode of this invention.

EXAMPLE I

A dry powdered color of intense yellow color was prepared by combining and thereafter dry blending a 1:2 weight ratio of ferric chloride and quinic acid. On blending, a rich yellow colored powder was obtained. This was dry blended with the remaining dry ingredients of a dry beverage mix and stored in a sealed jar for about 3 weeks. However, after the 3 week period, small, sticky spots were apparent on the dry powder due, it is thought, to some type of reaction due to the presence of the ferric salt.

It has been determined that if one or both components of the color complex are co-dried as by freeze drying with a soluble carbohydrate, i.e., if the ferric salt alone or the acid alone or both α-hydroxy carboxylic acid and ferric salt are co-dried with the carbohydrate, a more stable, non-hygroscopic, dry-colored powder is obtained.

This further improvement of the immediate invention is the subject of a patent application herein incorporated by reference entitled "Stabilization of Iron Complexes As Food Colors," General Foods Corporation Docket No. authored by Dr. Thomas H. Parliment and being filed concurrently with immediate application.

EXAMPLE II

A prototype lemonade beverage product was prepared by co-freeze drying an aqueous solution of a 1:10 weight ratio of $FeCl_3$ with 10 D.E. Morex. The freeze dried iron powder was then combined with the following dry ingredients in 100 ml of water, all percentages given indicating percent by weight of the dry ingredients.

| | | gm per 100 ml |
|---|---|---|
| Iron required, $FeCl_3 \cdot 6 H_2O$ | | 0.016 |
| (Amount of ferric ion necessary) | | |
| Freeze dried iron powders | 1.6% | 0.160 |
| Quinic acid | 0.1% | 0.010 |
| Adipic acid | 4.8% | 0.470 |
| Sugar | 93.0% | 9.000 |
| Lemon juice | 0.05% | 0.005 |
| Lemon flavor | 0.15% | 0.015 |
| Hi Opacity Cloud | 0.3% | 0.030 |

The resultant dry beverage fortified powder was a light yellow color and, when dissolved in water, gave a typical lemon hue with no off flavor indicating that the color is compatible with beverage flavoring compounds.

EXAMPLE III

The same prototype lemonade product as in Example I was prepared except that the entire color complex rather than the iron component was dried on a soluble carbohydrate. This entailed freeze drying 0.8 gm $FeCl_3 \cdot 6 H_2O$ plus 0.5 gm. Quinic acid per 2.5 gm Morex in water.

The following formulation was prepared based on the percent by weight of dry ingredients.

| | per 100 ml | % |
|---|---|---|
| Freeze-dried color | .050 gm | 0.5 |
| Adipic acid | 0.470 | 4.9 |
| Sugar | 9.000 | 94.0 |
| Lemon flavor | 0.015 | 0.15 |
| Lemon juice | 0.005 | 0.05 |
| High opacity cloud | 0.030 | 0.3 |
| | 9.570 | |

The color of the freeze dried powder was lemon yellow as was the reconstituted product having a pH of 2.8. The flavor of the product was found to be most acceptable and the lemon colored product was stable for days at room temperature.

It will be appreciated that the various examples, conditions, and the like are intended for illustrative purposes and that obvious variations and modifications may be made without departing from the scope and spirit of the invention as defined in the appended claims.

Having thus described my invention, what is claimed is:

1. A new yellow color composition consisting essentially of a ferric salt and combinations thereof complexed with at least an equimolar amount of an α-hydroxy carboxylic acid having at least one and no more than 2 carboxyl functions for each hydroxyl group with a degree of conjugation in all instances not exceeding three double bonds and water soluble derivatives of said hydroxy acids wherein the α-hydroxy and carboxyl functions are not reacted.

2. The composition of claim 1 wherein the α-hydroxy-carboxylic acid is selected from the group consisting of quinic acid, mandelic acid and combinations thereof.

3. The composition of claim 1 wherein the ferric salt and α-hydroxy carboxylic acid, or chemical derivative thereof are in the respective molar ratio of 1:1 to 1:3.

4. The composition of claim 1 wherein the ferric salt is selected from the group consisting of ferric chloride, ferric sulfate and ferric nitrate.

5. A method of imparting to edible materials an intense yellow color which comprises adding to said edible materials a ferric salt and combinations thereof complexed with at least an equimolar amount of an α-hydroxy carboxylic acid having at least one and no more than 2 carboxyl functions for each α-hydroxyl group with a degree of conjugation in all instances not exceeding three dobule bonds, the amount of yellow color complex added being that amount effective to impart yellow color to said edible materials.

6. The method of claim 5 wherein the α-hydroxy carboxylic acid is selected from the group consisting of quinic acid, mandelic acid and combinations thereof.

7. The method of claim 5 wherein the ferric salt and hydroxy carboxylic acid, or chemical derivative thereof are in the respective molar ratio of 1:1 to 1:3.

8. The method of claim 5 wherein the ferric salt is selected from the group consisting of ferric chloride, ferric sulfate and ferric nitrate.

* * * * *